United States Patent [19]
Crittenden

[11] Patent Number: 4,896,670
[45] Date of Patent: Jan. 30, 1990

[54] KISSING BALLOON CATHETER

[75] Inventor: James F. Crittenden, Hollis, N.H.

[73] Assignee: C. R. Bard, Inc., Murray Hill, N.J.

[21] Appl. No.: 183,673

[22] Filed: Apr. 19, 1988

[51] Int. Cl.$^4$ ............................................. A61M 29/02
[52] U.S. Cl. ........................................ 606/194; 604/96
[58] Field of Search ................................. 604/96–103; 122/344, 341, 348.1, 672, 748

[56] References Cited

U.S. PATENT DOCUMENTS

| | | | |
|---|---|---|---|
| 3,692,018 | 9/1972 | Goetz et al. | 128/344 X |
| 3,911,927 | 10/1975 | Rich et al. | 128/349 R |
| 3,939,820 | 2/1976 | Grayzel | 128/344 X |
| 4,413,989 | 11/1983 | Schjeldahl et al. | 604/96 |
| 4,456,011 | 6/1984 | Warnecke | 604/101 X |
| 4,753,238 | 6/1988 | Gaiser | 604/101 X |
| 4,777,951 | 10/1988 | Cribier et al. | 604/96 X |

Primary Examiner—Stephen C. Pellegrino
Attorney, Agent, or Firm—Wolf, Greenfield & Sacks

[57] ABSTRACT

A balloon dilatation catheter for use in percutaneous transluminal coronary angioplasty has a balloon having proximal and distal segments in which the proximal segment of the balloon is smaller in diameter than the distal segment. The catheter is adapted for use in the "kissing balloon" technique. The smaller diameter proximal sections reduce the distension of the common artery and bifurcation where the kissing balloon technique is utilized.

6 Claims, 2 Drawing Sheets

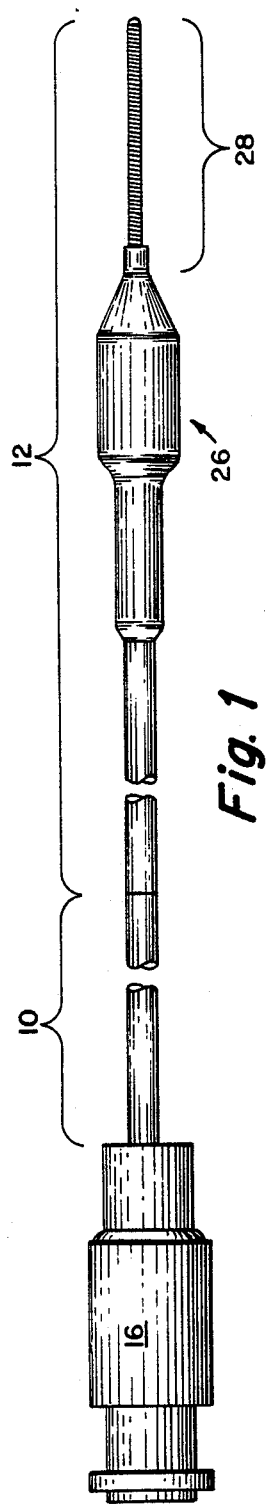
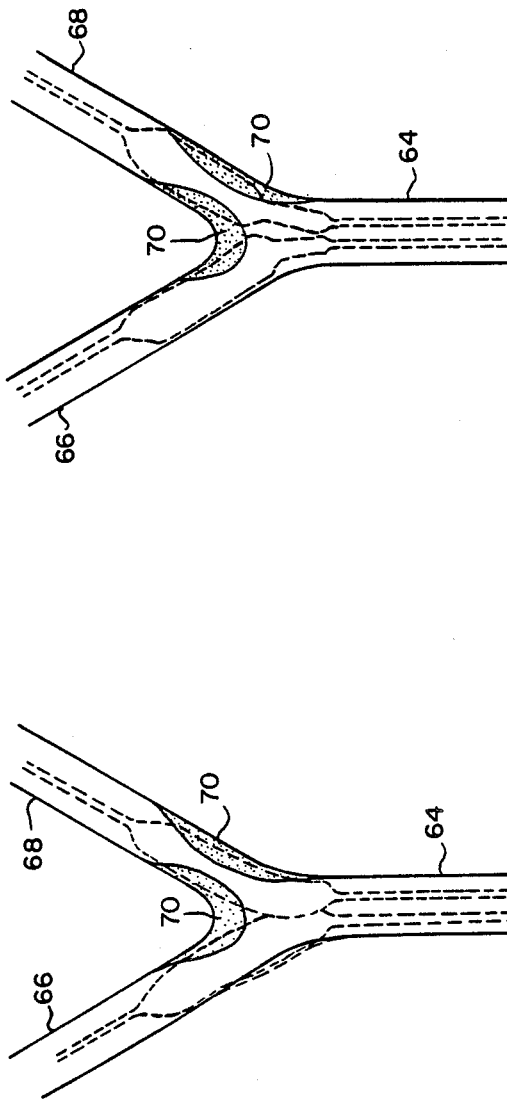
Fig. 1
Fig. 2
Fig. 3

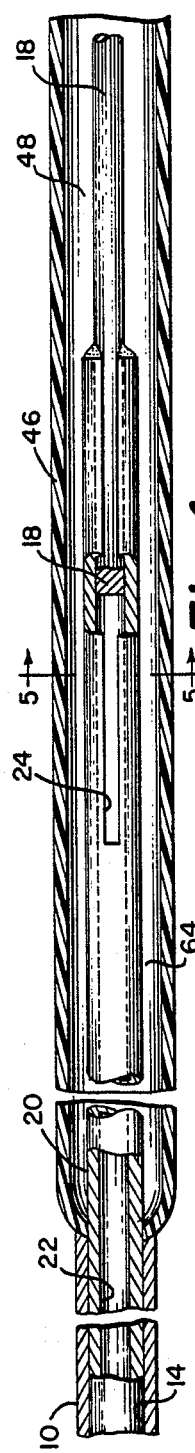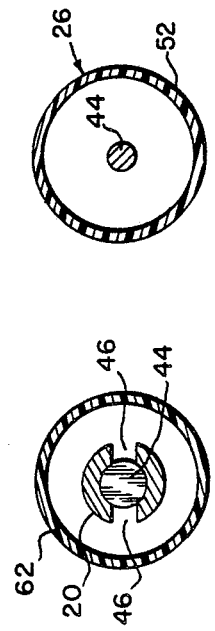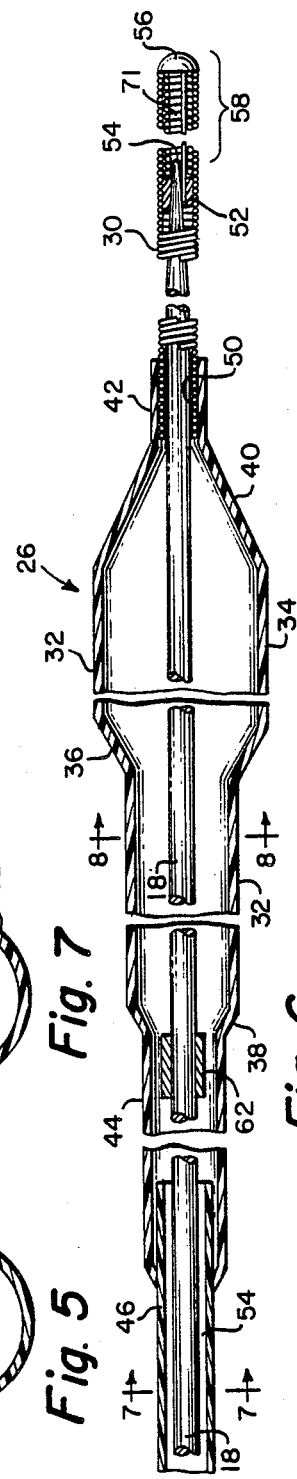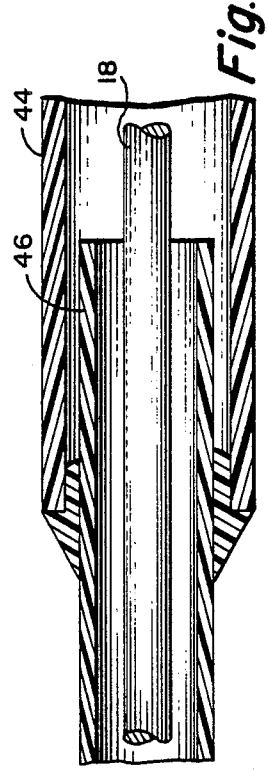

KISSING BALLOON CATHETER

FIELD OF THE INVENTION

This invention relates to catheters used in percutaneous transluminal coronary angioplasty.

BACKGROUND OF THE INVENTION

Percutaneous transluminal coronary angioplasty involves percutaneous introduction of a balloon catheter into an obstructed coronary artery and then inflating the balloon within the obstruction to widen the luminal passage through the artery to improve blood flow through the artery. Among the techniques that have developed is the "kissing balloon" technique which is used to treat an obstruction in the region of a bifurcation of an artery. Difficulty may arise when attempting to perform a dilatation in one of the branches of the bifurcated artery. In such a situation, the inflation of the balloon dilatation catheter in one artery may cause closure of the other adjacent branch artery. In order to prevent that occurrence, the "kissing balloon" technique was developed. In that technique, two balloon dilatation catheters are used, side-by-side, one catheter extending into one branch of the bifurcation and the other catheter extending into the other branch of the bifurcation. If the dilatation of the stenosed branch causes the other branch artery to become constricted, the balloon in that other branch then can be inflated to prevent closure of that other branch. Typically, in such an arrangement, the proximal ends of the balloons are disposed within the common trunk artery and their proximal ends touch or "kiss". The difficulty with this arrangement, however, is that when both balloons are inflated, the effective diameter at their proximal, kissing, ends may be too large for the diameter of the common trunk artery, thus, risking injury to that common artery. It is among the general objects of the present invention to provide an improved catheter construction that reduces the risk of damage to the common artery.

SUMMARY OF THE INVENTION

In accordance with the present invention, a catheter is provided having a shaft with a lumen extending along its length. The proximal end of the shaft carries a fitting through which a syringe can communicate with the inflation/deflation lumen that extends through the shaft. The distal end of the catheter carries a stepped diameter balloon that communicates with the inflation/deflation lumen. The stepped balloon has a proximal segment that is of a smaller diameter than the more distal segment. This arrangement enables a pair of such catheters to be used in a kissing balloon angioplasty technique in a manner that avoids the risk of injury to the trunk blood vessel. The proximal "kissing" ends of the balloon thus are defined by a pair of smaller diameter segments which, when inflated adjacent each other will present a reduced inflated area with reduced risk to the patient.

It is among the general objects to provide a balloon dilatation catheter adapted for use in the kissing balloon technique.

Another object of the invention is to provide a balloon dilatation catheter having a stepped balloon including a smaller diameter proximal segment and a larger diameter distal segment.

A further object of the invention is to provide a balloon dilatation catheter of the type described in which the risk of injury to a trunk coronary artery during a kissing balloon technique is reduced.

DESCRIPTION OF THE DRAWINGS

The foregoing and other objects an advantages of the invention will be appreciated more fully from the following further description thereof, with reference to the accompanying drawings wherein:

FIG. 1 is a fragmented illustration of the balloon dilatation catheter in accordance with the invention;

FIG. 2 is a diagrammatic illustration of the kissing balloon technique utilizing balloon dilatation catheters presently available;

FIG. 3 is an illustration of the kissing balloon technique utilizing a pair of catheters in accordance with the invention;

FIG. 4 is a sectional illustration of a segment of the catheter;

FIG. 5 is a sectional illustration of the catheter as seen along the line 5—5 of FIG. 4;

FIG. 6 is a fragmented sectional illustration of the distal portion of the catheter including the stepped balloon;

FIG. 7 is a sectional illustration through the catheter as seen along the line 7—7 of FIG. 6;

FIG. 8 is a sectional illustration of the catheter as seen along the line 8—8 of FIG. 6; and FIG. 9 is an enlarged sectional illustration of a portion of the catheter as shown in FIG. 6.

DESCRIPTION OF THE PREFERRED EMBODIMENT

FIG. 1 illustrates the catheter which has a proximal end (at the left in the drawing) and a distal end (at the right in the drawing). The catheter has a relatively long proximal segment 10 which may be formed from narrow, solid wall tubing, such as hypodermic tubing. In the illustrative embodiment, the proximal segment 10 may be of the order of 150 cm long. In the illustrative embodiment, the proximal segment 10 may be rigid torsionally so that it can transmit rotation from its proximal to its distal end. The distal end preferably can be bent to a curve so that the device may be steered and directed as it is advanced through the patient's vasculature. The proximal segment 10 also is flexible and can bend longitudinally to follow the curvature of the patient's arterial system. Preferably, the proximal segment 10 of the catheter is sufficiently flexible so that it can bend to follow the curve of a patient's aortic arch which has a radius of the order of between 2.5 and 3.5 inches in an adult.

As shown more clearly in enlarged FIG. 4, in the preferred embodiment of the invention the hollow tubular proximal segment 10 may have an outer diameter of 0.018", a wall thickness of about 0.002" and an internal diameter passage 14 of 0.014". A conventional fitting 16 is attached to the proximal end of segment 10 to facilitate connection with an inflation/deflation device, such as a syringe (not shown).

The catheter includes a distal segment 12 which extends from the distal end of the proximal segment 10 to the distal end of the catheter. The distal segment 12 includes a narrow diameter elongate support wire 18 which is connected to and extends distally of the tubular proximal segment 10. The support wire 18 is connected to the proximal tubing 10 by a short transition tube 20. The transition tube 20 is about 3" long and also is formed from a slender, flexible hypodermic tubing with a smaller diameter than the proximal tube 10. In the illustrative embodiment, the transition tube 20 is formed from hypodermic tubing having an outer diameter of 0.014", a wall thickness of 0.003" and an inner diameter of 0.008". The proximal end of the tubing 20 is received within the distal end of the internal passage 14 of the proximal segment 10 and is secured thereto as by soldering or brazing. The solid support wire 18 is attached to the distal end of the transition tube 20. The wire 18, which in the illustrative embodiment is very slender, preferably 0.008" diameter, is received in the distal end of the passage 22 of the tubing 20 and is secured by soldering or brazing. The support wire 18 plugs the distal end of the tubing 20. The transition tube 20 is provided with apertures 24 on opposite sides of the tubed wall to provide communication with internal passages 22, 14 so as to provide communication with a balloon 26 mounted on the distal region of the catheter. The apertures 24 may be defined by forming a pair of longitudinal slots in the wall of the tubing 20.

The support wire 18 provides support for the balloon 26 and also extends distally beyond the balloon 26, to form the core of a leader segment 28. The leader segment includes a helically wound radiopaque coil spring 30 which is attached to the distal end of the core wire 18 as described below. The balloon 26 is formed by molding a high strength polymeric material in a manner which provides a thin balloon wall, not greater than about 0.001" thickness and preferably having a thickness of the order of 0.0005". The balloon may be manufactured as described in U.S. Pat. No. 4,490,421 issued Dec. 25, 1984 and reference is made thereto for further details concerning the manufacture of the balloon.

As shown in enlarged detail in FIG. 6, the balloon 26 is of a stepped configuration having a proximal section 32 that is of smaller diameter than a distal section 34. Both sections 32, 34 are cylindrical and are joined by a proximally tapering generally conical portion 36. By way of illustrative example, the balloon may have an overall length of about 25 mm, with the proximal segment being approximately 12 to 13 mm in length and about 2.0 mm in diameter and the distal segment being approximately 12 to 13 mm in length and 2.5 mm in diameter. The balloon is formed from a high strength material which will not tend to stretch when inflated. For example, polyethylene terephthalate is a desirable material for the balloon. The balloon is formed to include tapering portions 38, 40 at the proximal and distal ends respectively. The distal tapering portion 40 merges into a narrowed neck 42 which fits snugly about and against the proximal end of the coil spring 30. The distal neck 42 of the balloon 26 is adhesively attached to the coil spring 30. The proximal end of the coil spring 30 is soldered securely to the core wire 18 at the region where the distal neck 42 is joined. The proximal tapering portion 38 merges into a narrowed proximal neck 44.

In order to communicate the interior of the balloon 26 with the inflation/deflation passages 14, 22 of the tubing, an extension sleeve 46 is adhesively attached to the proximal neck 44. The extension sleeve 46 extends proximally over one support wire 18. The proximal end of the extension sleeve 46 preferably is formed from the same material as the balloon 26 and is securely and adhesively attached to the outer surface of the transition tube 20, where it joins the main tube 10. The extension sleeve 46 defines an annular passage 48 about the support wire 18. The annular passage 48 provides communication between the apertures 24 and the interior of the balloon 26 for inflation and deflation of the balloon.

As shown in FIG. 6, the leader segment 28 which extends distally of the balloon 26 is of increasing flexibility in a distal direction to provide a relatively soft flexible leading tip which reduces the chance of trauma or injury to the blood vessel. In the illustrative embodiment, the leader segment may be about 3 cm long. The coil spring 30 is soldered at its proximal end, to the support wire 18 as indicated at 50. The distal end of the support wire 18 also is soldered to the coil spring 30 as indicated at 52. Soldered joint 52 and the distal tip 54 of the support wire 18 terminate short of the distal tip 56 of the coil spring 30. The distal segment 58 of the coil spring 30 may extend about 5 mm beyond the soldered joint 52 and defines a highly flexible bumper tip. A rounded weld bead 56 forms and defines the distal tip of the spring 30. The leader segment 28 is of increasing flexibility in a distal direction. The support wire 18 is taper ground and, for example, may be ground smoothly to a 0.002" diameter at its distal tip 54.

The distal segment 58 of the coil spring 30 includes a flexible and bendable stainless steel shaping ribbon 60 which is secured to the distal tip 54 of the support wire at one end and to the distal weld bead 56 at its other end. The shaping ribbon is of slender, rectangular cross-section, of the order of 0.001" by 0.002". The shaping ribbon is adapted to be bent to a desired curve and to retain that curve when relaxed. The preset curve enables the catheter to be steered by rotation of the catheter from its proximal end to direct the bent distal tip in selective directions as desired within the patient's blood vessels.

The catheter also may be provided with a radiopaque marker band 62 which preferably is formed from platinum. The marker band 62 is located proximally of the main portion of the balloon 26. In the illustrative embodiment, it is securely attached to the support wire 18. The marker band 62 provides a means by which the physician can verify, fluoroscopically, the position of the catheter.

FIG. 2 illustrates the kissing balloon technique using conventional balloon catheters. FIG. 3 illustrates the manner in which the balloon dilatation catheter of the present invention is used in the kissing balloon technique. As shown diagrammatically in each of FIGS. 2 and 3, a bifurcated blood vessel has a trunk portion 64 and a pair of bifurcated blood vessels 66, 68 in communication with the trunk 64. The blood vessel 68 has a stenosis 70 adjacent the junction of the blood vessels. As is common, the stenosis may extend partially around the bifurcation and into the other blood vessel. In the kissing balloon technique illustrated in FIG. 2, a pier of balloon dilatation catheters are inserted through the trunk vessel 64 with one of the balloons being disposed in each of the vessels 66, 68. The proximal ends of the balloons typically remain in the trunk vessel 64 and contact or "kiss" each other. As illustrated in FIG. 2, when the balloons are inflated, that may tend to risk injury to the trunk vessel 64 from over inflation. As illustrated in FIG. 3, with the present invention, the proximal smaller diameter portions of the balloon are disposed in the trunk and will not over distend the trunk vessel 64.

It should be understood that although the invention has been illustrated in FIG. 3 utilizing two catheters of the present invention, the invention also may be practiced using a conventional balloon dilatation catheter together with one catheter having a balloon with a reduced proximal diameter in accordance with the invention, depending on the coronary anatomy of the particular patient.

Thus, the invention provides a dilatation catheter configuration adapted specifically for reduced risk in the practice of the kissing balloon technique. It should be understood that the foregoing description of the invention is intended to be illustrative thereof and that other embodiments and modifications may be apparent to those skilled in the art.

Having thus described the invention, what I desire to claim and secure by letters patent is:

1. A balloon dilatation catheter comprising:
    an elongate shaft having proximal and distal ends and having a lumen extending therethrough;
    a fitting on the proximal end of the shaft for connection with a source of fluid under pressure;
    a dilatation balloon adapted to be inflated to a predetermined size and mounted to the distal end of the shaft, the interior of the balloon being in communication with the lumen whereby the balloon may be inflated and deflated;
    the balloon being of unitary construction and having a proximal portion and a distal portion, the proximal portion of the balloon having a smaller inflated diameter than the distal portion of the balloon, each of said proximal and distal portions having a length, when inflated, at least twice that of its diameter, when inflated.

2. A balloon dilatation catheter comprising:
    an elongate shaft having proximal and distal ends and having a lumen extending therethrough;
    a fitting on the proximal end of the shaft for connection with a source of fluid under pressure;
    a dilatation balloon adapted to be inflated to a predetermined size and mounted to the distal end of the shaft, the interior of the balloon being in communication with the lumen whereby the balloon may be inflated and deflated;
    the balloon being of unitary construction and having a proximal portion and a distal portion, the proximal portion of the balloon having a smaller inflated diameter than the distal portion of the balloon, the balloon including a stepped construction having a pair of cylindrical portions connected to each other by a tapered transitional portion.

3. A balloon dilatation catheter as defined in claim 2 wherein each of the proximal portion and distal portion of the balloon has a length, when inflated, that is at least twice as long as its diameter, when inflated.

4. A method for dilating a stenosis in a coronary artery in the region of the juncture of a common artery with a pair of branch arteries comprising:
    providing a pair of balloon dilatation catheters, at least one of said balloon dilatation catheters having:
    an elongate shaft having proximal and distal ends and having a lumen extending therethrough;
    a fitting on the proximal end of the shaft for connection with a source of fluid under pressure;
    a dilatation balloon mounted to the distal end of the shaft, the interior of the balloon being in communication with the lumen whereby the lumen may be inflated and deflated;
    the balloon having a proximal portion and a distal portion, the proximal portion of the balloon having a smaller inflated diameter than the distal portion of the balloon,
    said method further comprising advancing both of said dilatation catheters through the common artery and into the branch arteries with the distal portion of one of said catheters extending into one of the branch arteries and a distal portion of the other of said catheters extending into the other of said branch arteries and with the proximal ends of said catheters being disposed in the common artery; and
    inflating at least one of said balloons to effect a dilatation of a stenosis in the region of the juncture of said common and branch arteries.

5. A method as defined in claim 4 wherein both of said catheters are inflated simultaneously.

6. A method as defined in claims 4 or 5 wherein both of said catheters have balloons with smaller diameter proximal portions.

* * * * *